United States Patent [19]

Saito et al.

[11] Patent Number: 5,008,350
[45] Date of Patent: Apr. 16, 1991

[54] GLYCIDYL ETHERS OF PHENOLIC COMPOUNDS AND PROCESS FOR PRODUCING THE SAME

[75] Inventors: Noriaki Saito; Shuichi Kanagawa; Hideshi Sakamoto, all of Niihama, Japan

[73] Assignee: Sumitomo Chemical Company, Limited, Osaka, Japan

[21] Appl. No.: 282,569

[22] Filed: Dec. 12, 1988

[30] Foreign Application Priority Data

Dec. 16, 1987 [JP] Japan .................................. 62-319289
Dec. 26, 1987 [JP] Japan .................................. 62-331287

[51] Int. Cl.$^5$ ............................................. C08G 59/32
[52] U.S. Cl. ...................................... 525/507; 525/482
[58] Field of Search ...................... 525/109, 482, 507

[56]  References Cited

U.S. PATENT DOCUMENTS

| | | | |
|---|---|---|---|
| 4,390,664 | 6/1983 | Kanayama | 525/507 |
| 4,394,496 | 6/1983 | Schrader | 528/98 |
| 4,468,508 | 8/1984 | Ito et al. | 525/507 |
| 4,551,508 | 11/1985 | Urasaki | 528/97 |
| 4,778,863 | 10/1988 | Wang et al. | 528/95 |

FOREIGN PATENT DOCUMENTS 3264622 11/1988 Japan ................................ 528/98

Primary Examiner—John Kight, III
Assistant Examiner—Frederick Krass
Attorney, Agent, or Firm—Stevens, Davis, Miller & Mosher

[57]  ABSTRACT

A glycidyl ether of a phenolic compound of the formula:

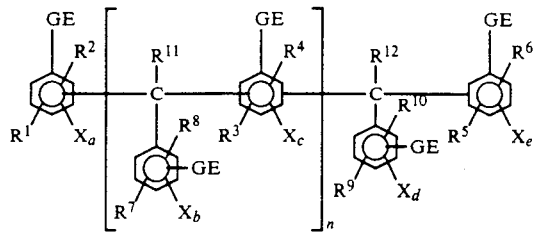

wherein each of $R^1$ through $R^6$ represents an alkyl group of from 1 to 6 carbon atoms; each of $R^7$ to $R^{12}$ represents a hydrogen atom, an alkyl group of from 1 to 4 carbon atoms, or an alkoxy group of from 1 to 4 carbon atoms; X represents a chlorine or bromine atom ; GE represents a glycidyl ether group; a, b, c, d, and e are 0 or 1; and n is an average number of from 0.5 to 5. The high purity glycidyl ether of the phenolic compound can be produced by reacting the corresponding phenolic compound with an epichlorohydrin in an aprotic polar solvent in the presence of an alkali metal hydroxide and then treating the resulting crude glycidyl ether compound with an alkaline material in an organic solvent.

3 Claims, No Drawings

GLYCIDYL ETHERS OF PHENOLIC COMPOUNDS AND PROCESS FOR PRODUCING THE SAME

The present invention relates to an epoxy resin applied for the electric and electronic industries, particularly for encapsulating and laminating materials and also relates to a process for producing the epoxy resin.

In recent years the transfer moldings of epoxy resin compositions have been applied for encapsulating semiconductors such as LSIs, ICs, and transistors because of its high productivity and low cost. LSIs encapsulated by the epoxy resin compositions have been surface-mounted and directly submerged in the solder baths. A glycidyl ether of o-cresol novolac, which is mainly used today, has well-balanced properties, but the epoxy resin compositions thereof used to be cracked by the heat shock of the direct soldering process.

Epoxy resins for encapsulating electronic components are required to have a higher temperature performance and other well-balanced properties such as a moisture performance and a high purity, particularly a low hydrolyzable chlorine content.

A glycidyl ether of a tris(hydroxyphenyl)methane and alkyl-substituted products thereof exhibits a higher temperature performance.

A tris(hydroxyphenyl)methane is, however, liable to form a product of higher molecular weight or a gel through intermolecular reaction during the glycidyl etherification thereof. The higher molecular weight product of the intermolecular reaction has a too high epoxy equivalent weight and its cured products will have undesirably low crosslinking density and temperature performance.

To control the intermolecular reaction and obtain a resin of low epoxy equivalent weight, various methods have been taken up to now.

For instance, Industrial and Engineering Chemistry, Vol. 45, p. 2715 (1953) describes a process which comprises adding sodium salt of tris(hydroxyphenyl)methane into 5 moles of epichlorohydrin per mole of the phenolic hydroxyl groups.

According to this process, however, the epoxy content of the product is as low as 0.32 equivalent per 100 g (viz. the epoxy equivalent weight is as high as 313) and the product yield is also as low as 54%. Thus this process is not satisfactory.

U.S. Pat. No. 4,394,496 describes a twostep process which comprises reacting tris(hydroxyphenyl)methane with at least 10 moles of epihalohydrin per mole of the phenolic hydroxyl groups in the presence of a coupling catalyst in the first step and in the presence of a basic compound in the second step, thereby producing a glycidyl ether compound.

This process aims at raising the epoxy conversion of tris(hydroxyphenyl)methane, and the epoxy equivalent weight of the resultant glycidyl ether compound is 158, which is close to the theoretical value. This product, however, contains a very large amount of hydrolyzable chlorine, and hence is not satisfactory for use in the electric or electronic industry.

While this U.S. Patent discloses also an oligomeric compound resulting from intermolecular reaction and a process for producing the oligomer, it does not disclose any glycidyl ether compounds suitable for encapsulating electronic components at the present technical level.

Of glycidyl ethers of the tris(hydroxyphenyl)methane and alkyl-substituted products thereof, the compound having no alkyl substituent and compounds having a small number of lower alkyl substituents are highly hygroscopic and compounds having a large number of higher alkyl substituents show a poor temperature performance. Thus, it is necessary to develop a glycidyl ether compound having better balanced properties.

U.S. Pat. No. 4,390,664 discloses glycidyl ethers of phenolic compounds produced by the condensation of aromatic aldehydes with phenols such as phenol, alkyl-monosubstituted phenols, and halogen-substituted phenols. While the invention of this U.S. Patent aims at providing a glycidyl ether compound improved in high temperature performance over glycidyl ethers of tris(hydroxyphenyl)methane, the product compound is not low in hygroscopicity and moreover the glycidyl etherifying reaction is carried out according to the conventional method and therefore the product glycidyl ether compound has low purity and contains a large amount of hydrolyzable chlorine in particular.

The present invention involves a glycidyl ether of a phenolic compound of the formula (I):

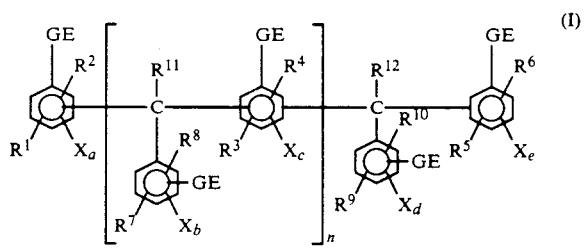

wherein each of $R^1$ through $R^6$ represents an alkyl group of from 1 to 6 carbon atoms; each of $R^7$ through $R^{12}$ represents a hydrogen atom, an alkyl group of from 1 to 4 carbon atoms, or an alkoxy group of from 1 to 4 carbon atoms; X represents a chlorine or bromine atom; GE represents a glycidyl ether group; a, b, c, d, and e are 0 or 1; and n is an average number of from 0.5 to 5.

Of the glycidyl ether compounds represented by formula (I), preferred in performance are compounds in which each of $R^1$, $R^3$, and $R^5$ is methyl, each of $R^2$, $R^4$, and $R^6$ is an alkyl group of from 3 to 6 carbon atoms, each of $R^7$, $R^8$, $R^9$, $R^{10}$, $R^{11}$, and $R^{12}$ is a hydrogen atom, and each of a, b, c, d, and e is 0, that is, compounds represented by the formula (II):

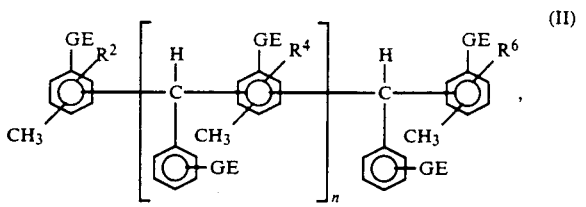

wherein each of $R^2$, $R^4$, and $R^6$ represents an alkyl group of from 3 to 6 carbon atoms, n is an average number of 0.5 to 5, and GE represents a glycidyl ether group.

Above all, a glycidyl ether compound represented by the formula (III):

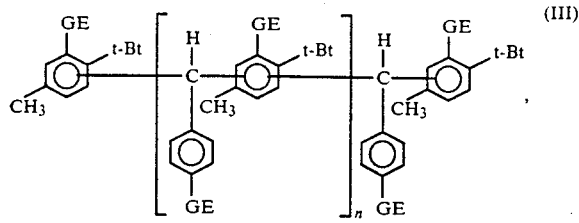

wherein t-Bt represents tertiary butyl group, n is an average number of 0.5 to 5, and GE represents a glycidyl ether group, is particularly preferred in view of the performance of the glycidyl ether compound itself, ease of the reaction to form itself, and ease of obtaining the raw materials industrially.

When the number of alkyl substituents attached to aromatic rings and the number of carbon atoms in each alkyl substituent are relatively small, such glycidyl ether compounds are highly hygroscopic. On the contrary, when the number of said alkyl substituents and the number of said carbon atoms are relatively large, such compounds have poor temperature performance. Chlorine or bromine atom represented by X imparts flame retardance. As an increase in the average number n of repeating units, the temperature performance is improved but the viscosity increases and this causes poor moldability and processability. On the contrary, as a decrease in the average number n of repeating units, the temperature performance is not enough improved. Hence, the value of n is desired to be in the range of from 0.5 to 5.

The glycidyl ether of a phenolic compound can be produced by reacting the corresponding phenolic compound with an epichlorohydrin. The phenolic compound corresponding to the glycidyl ether compound of the formula (I) is represented by the formula (IV):

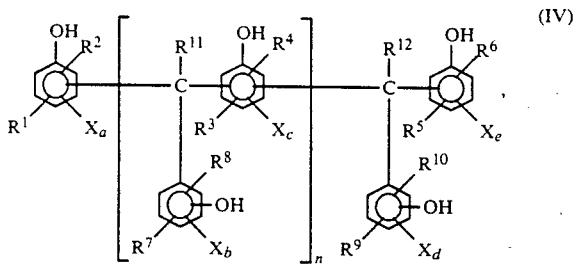

wherein the simbols are the same as those in the formula (I).

The phenolic compound of the formula (IV) can be produced by the condensation of phenols with hydroxy aromatic carbonyl compounds by applying the well known novolak synthesizing reaction. This reaction is carried out at a temperature of 0° to 180° C. in the presence of a well known acid catalyst for novolak synthesis. Such catalysts include mineral acids, e.g., hydrochloric acid, sulfuric acid, and phosphoric acid; organic acids, e.g., oxalic acid and toluenesulfonic acid; and salts, e.g., zinc acetate. For this reaction may be used an aromatic solvent such as toluene or chlorobenzene.

The molar ratio of the hydroxy aromatic carbonyl compounds to the phenols is approximately from 0.3:1.0 to 1.0:1.0.

In order to achieve a larger average number n of repeating units, it is necessary to carry out the reaction by using a higher proportion of the hydroxy aromatic carbonyl compound at a somewhat higher termperature in the presence of a larger amount of catalyst.

Suitable alkyl-substituted phenols include phenols substituted by two alkyl groups of from 1 to 6 carbon atoms and chlorine- or bromine-substituted products of these dialkyl phenols Preferably, one of the two alkyl substituents is methyl and the other is an alkyl group of from 3 to 6 carbon atoms. Examples of the preferable dialkylphenols are methylpropylphenol, methylpentylphenol, methylbutylphenol, and methylhexylphenol. Above all, methyl-tert-butylphenol is most desirable in view of the glycidyl etherifying reaction as well as the performance of the product glycidyl ether compound.

These dialkylphenols may be used alone or in combination. Small amounts of other phenols, e.g., phenol, cresol, resorcinol, catechol, and bisphenol A, can be used additionally for the purpose of further imparting various desirable properties.

Suitable hydroxy aromatic carbonyl compounds include hydroxy aromatic ketones and hydroxy aromatic aldehydes, for example, hydroxyacetophenone, methylhydroxyacetophenone, methoxyhydroxy acetophenone, hydroxybenzaldehyde, methylhydroxybenzaldehyde, methoxy hydroxy benzaldehyde, dimethylhydroxybenzaldehyde, chlorohydroxybenzaldehyde, and bromohydroxybenzaldehyde. Of these compounds, preferred is hydroxybenzaldehyde and particularly preferred is p-hydroxybenzaldehyde in view of the performance of the product. Two or more of these hydroxy aromatic carbonyl compounds may be used in combination and further with small amounts of other aldehydes such as formaldehyde, acetoaldehyde, acrolein, croton aldehyde, benzaldehyde, and glyoxal.

Phenolic compounds of the present invention can be also given the substituents by the alkylation, chlorination, or bromination reaction to the condensation products of phenols and hydroxy aromatic carbonyl compounds. The phenolic compounds substituted by alkyl groups are expected to improve moisture performance and the compounds substituted by chlorine or bromine atom are expected to improve inflammability.

The reaction of the phenolic compound with an epichlorohydrin to produce the glycidyl ether compound is generally carried out in the presence of an alkali metal hydroxide. Among various improved techniques for obtaining high-purity glycidyl ethers, the process of the present invention is characterized by reacting a phenolic compound as specified above with an epichlorohydrin in the presence of an aprotic polar solvent in addition to the alkali metal hydroxide, then removing the unreacted materials, the alkali metal salt and water as the by-products, and the aprotic polar solvent, and treating the resulting crude glycidyl ether of the phenolic compound with an alkaline material in an organic solvent, thereby yielding a high-purity glycidyl ether of a phenolic compound.

For the reaction, epichlorohydrin is used in an amount of about 2.5 to 8 moles per mole of the phenolic hydroxyl groups.

The use of epichlorohydrin in less amounts than the above lower limit is undesirable, because this results in such industrial disadvantages that the intermolecular reaction produces a high polymer to cause a rise in the melt viscosity of the product glycidyl ether compound, the deterioration of product resin quality, and further an increase in the amount of gel formed. The use of more epichlorohidrin than the above upper limit is also undesirable, since this merely increases the volume of the reaction mixture to result in industrial disadvantages such as lowering of the productivity.

Suitable alkali metal hydroxides for use in the present invention are, for example, sodium hydroxide and potassium hydroxide, though not limited to these hydroxides. The amount of alkali metal hydroxide used is desired to be about one equivalent to the phenolic hydroxyl groups. When the amount of alkali metal hydroxide used is less than about one equivalent, some of the phenolic hydroxyl groups remain unreacted and hence the intermolecular reaction takes place to form a high polymer, which is undesirable. When the amount of alkali metal hydroxide used is more than about one equivalent, an increased amount of gel is produced to bring about disadvantages in the production process.

An aqueous solution of the alkali metal hydroxide, higher concentrations of which are preferable, is used since water must be removed from the reaction mixture.

Suitable aprotic polar solvents for use in the present invention include, for example, dimethylsulfoxide, dimethyl sulfone, dimethylacetamide, tetramethylurea, and hexamethylphosphorylamide.

These aprotic polar solvents are used in an amount of 20 to 100 parts, preferably 40 to 80 parts, by weight based on 100 parts by weight of epichlorohydrin used. When the solvent is used in too small amounts, the content of hydrolyzable chlorine in the product is not notably reduced and moreover phenolic hydroxyl groups remain unreacted. This is undesirable as stated above. When the solvent is used more than the above amount, the intermolecular reaction proceeds to result in low product quality as well as low productivity, which is undesirable.

In the present invention, the glycidyl etherification of said phenolic compound can be carried out, for instance, as follows:

First, a uniform solution is prepared by mixing together said polyhydric phenol, epichlorohydrin, and said aprotic polar solvent in proportions as stated above. Then, said alkali metal hydroxide (dissolved in water) is added to the solution with stirring to initiate the reaction. This reaction is conducted in the temperature range of 20° to 80° C., preferably 30° to 70° C.

In the case of the present invention, the reaction temperature has large influences. That is, in decreasing temperature, the selectivity of the reaction rises and the content of hydrolyzable chlorine decreases. At too low temperatures the reaction rate is, however, undesirably low to decrease the productivity. At temperatures exceeding 80° C., the effect of the present invention is limited and the intermolecular reaction is undesirably promoted.

During this reaction, volatile matters are evaporated from the reaction mixture under reduced pressure and condensed, the condensate is separated into an oil phase and a water phase, and the oil phase is returned to the reaction system, whereby the dehydration is performed. In this operation, the temperature and pressure are set under such conditions that the water content in the reaction system may be from 0.5 to 5.0%, preferably from 0.5 to 3.0%, by weight. Excessive contents of water in the reaction system have such adverse effects that the product contains a large amount of hydrolyzable chlorine and has a high epoxy equivalent weight and moreover that much epichlorohydrin is wasted by hydrolysis. The pressure is necessarily fixed when the temperature is set according to the composition of the reaction mixture.

To carry out the reaction uniformly, the alkali metal hydroxide is added intermittently in small amounts or continuously at a low rate over 2-7 hours. Adding the alkali metal hydroxide momentarily or quickly causes the reaction to proceed locally, resulting in gel formation and/or making it impossible to maintain the predetermined concentration of water, which is not desirable.

After finish of the reaction, the unreacted materials and by-products are removed in conventional or well known methods. That is, the unreacted epichlorohydrin and remaining water are removed by distillation, and the residue containing the glycidyl ether compound is mixed with an organic solvent selected from ketone solvents such as methyl isobutyl ketone and methyl ethyl ketone and aromatic solvents such as benzene and toluene to dissolve the glycidyl ether compound. The alkali metal salt, which is insoluble, is removed by filtration or washing with water. The aprotic polar solvent is removed by washing with water.

While a crude glycidyl ether compound can be obtained by evaporating the organic solvent from the above solution, this solution containing a crude glycidyl ether compound, according to the present invention, is further treated with an alkaline material.

Suitable alkaline materials for this treatment include alkali metal hydroxides, alkaline earth metal hydroxides, and alkali metal carbonates, for example, sodium hydroxide, potassium hydroxide, calcium hydroxide, sodium carbonate, and potassium carbonate.

The alkaline material is used in an amount of 0.01 to 0.10 mole per mole of the phenolic hydroxyl groups.

When the amount of alkaline material used is less than the above lower limit, the content of hydrolyzable chlorine is not reduced effectively. When the amount exceeds the above upper limit, the polymerization through the intermolecular reaction tends to take place The alkaline material in the form of fine powders or aqueous solution is mixed with the solution of the glycidyl ether compound in the organic solvent and reacted at 40°-100° C. for 30 minutes to several hours.

At temperatures below 40° C. the content of hydrolyzable chlorine is not reduced effectively, while at temperatures above 100° C. the polymerization is liable to take place.

The excess alkaline material is neutralized with phosphoric acid, carbon dioxide gas or the like, and the resulting salt is removed by filtration or washing with water, and then the organic solvent is removed by distillation to recover the intended high-purity glycidyl ether of a phenolic compound.

The glycidyl ether of a phenolic compound of the present invention can be mixed with hardeners to provide epoxy resin compositions. These compositions can be used extensively to form epoxy resins having high temperature performance, low hygroscopicity, and good mechanical properties.

The above hardeners include polyhydric phenols such as phenol novolak, cresol novolak, polyvinylphenol and the phenolic compound of the formula (IV); amine type curing agents such as diaminodiphenylmethane and diaminodiphenyl sulfone; and acid anhydride type curing agents such as pyromellitic anhydride, trimellitic anhydride, and benzophenonetetracarboxylic dianhydride. In general, these hardeners are selected according to the individual applications of cured epoxy resins. Polyhydric phenols are fitted for encapsulation purposes and amines are fitted for laminated board production. These hardeners are used in amounts of 0.7 to 1.2 equivalents to the epoxy groups contained in the glycidyl ether compound. When the amount is less than 0.7 equivalent or more than 1.2 equivalents to the epoxy groups, the curing is imperfect and the cured product will not be low hygroscopic.

Depending on the product applications, known suitable additives can be incorporated into the epoxy resin compositions. Such additives include fillers, accelerators, flame retardants, mold-releasing agents, surface treating agents and the like.

Fillers include silica, alumina, talc, clay, and glass fiber; accelerators include imidazole compounds, tertiary amines, and phosphoric compounds; and flame retardants include brominated epoxy resins and antimony trioxide. Mold-releasing agents include waxes and metal salts of higher fatty acids including zinc stearate; and surface treating agents include silane coupling agents.

When used as an encapsulating material, the epoxy resin composition may contain various elastomers for the purpose of lowering the stress which will be caused in the cured composition. Such elastomers include, for example, polybutadiene rubber, butadiene-acrylonitrile copolymer, and silicone rubber.

For encapsulating electronic components such as semiconductor devices with the resin composition of the present invention, the composition is cured according to the conventional known molding method such as transfer molding, compression molding, or injection molding.

For the fabrication of laminated boards by using the resin composition of the present invention, glass fibers or organic fibers are impregnated with a uniform solution of the composition in a solvent such as methyl ethyl ketone, toluene or ethylene glycol monomethyl ether and then dried by heating to form prepregs, which are then compression-molded.

The glycidyl ether compound of the present invention can provide epoxy resin compositions which, as encapsulants for electronic components and as laminated board materials, can be cured into moldings having low hygroscopicity and temperature performance durable for use at higher temperatures. These compositions have improved processability and can be molded into cured products of higher reliability.

According to the process of the present invention, high-purity glycidyl ether compounds of low hydrolyzable chlorine contents and small epoxy equivalent weights can be obtained industrially with good productivity.

The present invention is illustrated with reference to the following examples.

In the examples, the epoxy equivalent weight is defined as the molecular weight of the epoxy resin per epoxy group.

The hydrolyzable chlorine content was determined by dissolving a sample of epoxy resin in dioxane, adding an alcoholic solution of potassium hydroxide, heating the mixture under reflux for 30 minutes, and titrating the released chlorine ions with a silver nitrate solution. The found value was expressed in the parts per million based on the epoxy resin.

The water content in the reaction system was measured by the Karl Fischer's method.

The average number of repeating units was calculated from the average molecular weight determined by using a gel permeation chromatograph (TRIROTAR SR-II manufactured by Japan Spectroscopic Co., Ltd.).

Properties of cured products were evaluated as follows:

Glass transition temperature: Measured by using a thermal mechanical analyzer (Model TMA 10 manufactured by Daini Seikosha Co., Ltd.).

Flexural strength and flexural modulus: Measured in accordance with JIS K-6911 by using an Instron universal material tester (INSTRON Model 1122).

Boiling water absorption: The change in the weight of a test specimen was measured under the conditions: temperature 121° C., pressure 2 atm., and period 75 hours, by using a high-pressure steam environment tester (Model PC-305S manufactured by Hirayama Seisakusho Co., Ltd.).

REFERENTIAL EXAMPLES 1-6 AND COMPARATIVE REFERENTIAL EXAMPLES 1-6

Each of phenols, the names and amounts of which are shown in Table 1, 122 g of p-hydroxybenzaldehyde, and 3.8 g of p-toluene sulfonic acid (monohydrate) were reacted together in a reactor equipped with a thermometer, stirrer, and condenser under reflux with stirring at 95°-105° C. for 6 hours.

Thereafter, each of the reaction mixtures was neutralized with a 10% aqueous sodium hydroxide solution, and washed twice with water. Then, the unreacted monomers were removed by distillation to yield a reddish brown phenolic compound. The average numbers of repeating units of the resulting phenolic compounds are shown in Table 1.

TABLE 1

|  | Phenols | | Average number of repeating units |
|---|---|---|---|
|  | Name | Amount (g) |  |
| Referential Example | | | |
| 1 | 3-Methyl-6-t-butylphenol | 328 | 1.7 |
| 2 | 3-Methyl-6-t-butylphenol | 295.2 | 2.8 |
| 3 | 3-Methyl-6-t-butylphenol | 262.4 | 4.1 |
| 4 | 4-Methyl-2-t-butylphenol | 328 | 1.9 |
| 5 | 5-Methyl-2-isopropylphenol | 300 | 1.6 |
| 6 | 2-Methyl-4-n-hexylphenol | 384 | 2.0 |
| Comparative Referential Example | | | |
| 1 | Phenol | 1410 | 0.3 |
| 2 | Phenol | 188 | 3.3 |
| 3 | o-Cresol | 216 | 2.1 |
| 4 | 4-t-Butylphenol | 300 | 2.3 |
| 5 | 3-Methyl-6-t-butylphenol | 1640 | 0.2 |

TABLE 1-continued

| | Phenols | | Average number of repeating |
|---|---|---|---|
| | Name | Amount (g) | units |
| 6 | 2-Methyl-4-nonylphenol | 468 | 2.4 |

REFERENTIAL EXAMPLE 7

A phenolic compound was prepared according to the procedures of Referential Example 1 except using 246 g of 3-methyl-6-t-butylphenol and 54 g of m-cresol in place of 328 g of 3-methyl-6-t-butylphenol. The average number of repeating units of the resultant compound was 2.2.

REFERENTIAL EXAMPLE 8

246 g of 3-methyl-6-t-butylphenol, 54 g of o-cresol, and 3.8 g of p-toluenesulfonic acid (monohydrate) were mixed in the same reactor as Referential Example 1, and then 16.7 g of a 36% aqueous solution of formaldehyde was added dropwise for an hour at a temperature of 95°-105° C., the mixture being maintained for one hour with stirring.

97.5 g of p-hydroxybenzaldehyde was added into the mixture and reacted for six hours under reflux. Then the same after-treatment as Referential Example 1 was carried out to obtain a phenolic compound.

The average number of repeating units was 2.2 (each of the numbers of repeating units derived from p-hydroxybenzaldehyde and formaldehyde was 1.8 and 0.4 respectively.).

EXAMPLES 1–10 AND COMPARATIVE EXAMPLES 1–6

Each of the phenolic compounds was reacted with an epichlorohydrin (names and amounts of the phenolic compounds and amounts of epichlorohydrin are shown in Table 2) in a separable flask equipped with a baffle, thermometer, stirrer, and further a dropping funnel for continuous addition of a 40% aqueous sodium hydroxide solution and a condenser-equipped tubular separator for cooling and liquefying the water and epichlorohydrin vaporized from the reaction system, separating the condensed liquids into an organic layer and a water layer by utilizing the specific gravity difference, and returning the organic layer into the reaction system while excluding the water layer.

This reaction was carried out in the presence of dimethylsulfoxide as an aprotic polar solvent, while adding continuously said sodium hydroxide solution over 4 hours, the amounts of said solvent and sodium hydroxide solution being shown in Table 2.

After finish of the reaction, the unreacted epichlorohydrin was removed by distillation under reduced pressure, and the residue was dissolved in 500 g of methyl isobutyl ketone. This solution was washed three times with 120 g of water to remove the by-product salt and the aprotic polar solvent.

Further, a 10% aqueous sodium hydroxide solution, the amount of which is shown in Table 2, was added in about 10 minutes to the methyl isobutyl ketone solution while keeping the temperature at 80° C. After 2 hours' standing, the resulting mixture was neutralized by blowing carbon dioxide gas thereinto. The resultant by-product salt was removed by filtration and then the solvent was removed by distillation. Thus, glycidyl ethers of the polyhydric phenols were obtained. Table 2 shows properties (hydrolyzable chlorine contents and epoxy equivalent weights) of these products.

COMPARATIVE EXAMPLE 7

A glycidyl ether compound was prepared according to the procedures of Example 1 except that, after glycidyl etherification, the solvent was immediately removed from the methyl isobutyl ketone solution of the crude glycidyl ether compound without adding the 10% aqueous sodium hydroxide solution.

Results of evaluation on properties of the product are shown in Table 2.

COMPARATIVE EXAMPLE 8

A glycidyl ether compound was prepared according to the procedures of Example 1 except using no aprotic polar solvent.

Results of evaluation on properties of the product are shown in Table 2.

COMPARATIVE EXAMPLE 9

Glycidyl etherification of the phenolic compound prepared in Referential Example 1 was carried out according to the method described in Example 3 of U.S. Pat. No. 4,394,496.

That is, 144.0 g of the phenolic compound prepared in Referential Example 1 and 925 g of epichlorohydrin were charged into a separable flask equipped with a baffle, thermometer, stirrer, and condenser. After dissolution of the phenolic compound, the solution was heated to the reflux temperature, and further 1.44 g of a 60% aqueous solution of benzyltrimethylammonium chloride was added. The mixture was maintained at the same temperature (119°-120° C.) for 1 hour and then cooled to 50° C. At this temperature, 333.3 ml of 3 molar NaOH in saturated $Na_2CO_3$ aqueous solution was added and reacted for 1 hour.

The resulting mixture was allowed to stand, and then the separated aqueous layer was removed, and further 166.7 ml of 3 molar NaOH in saturated $Na_2CO_3$ aqueous solution was added and reacted at 50° C. for 1 hour.

The resulting mixture was again allowed to stand, and the separated aqueous layer was removed, and then the organic layer was washed with 300 ml of a 1 wt. % aqueous acetic acid solution and further 5 times with 300 ml of pure water. Then, the unreacted epichlorohydrin was removed by distillation under reduced pressure to produce a glycidyl ether compound.

The epoxy equivalent weight of this product was 216 and the hydrolyzable chlorine content therein was 1080 ppm.

TABLE 2

|  | Phenolic compound | | Amount of Epichlorohydrin (g) | Amount of dimethylsulfoxide (g) | Amount of 40% aq. NaOH soln. (g) | Reaction temp./pressure (°C./Torr) | Water content in reaction system (%) | Amount of 10% aq. NaOH soln. (g) | Hydrolyzable chlorine content (ppm) | Epoxy equivalent weight |
|---|---|---|---|---|---|---|---|---|---|---|
|  | Source | Amount (g) | | | | | | | | |
| Ex. | Referential Example | | | | | | | | | |
| 1 | 1 | 144.0*1 | 370*2 | 148 | 100*3 | 45/38 | 1.9 | 20*4 | 140 | 219 |
| 2 | 2 | " | " | " | " | " | 2.0 | " | 150 | 216 |
| 3 | 3 | " | " | " | " | " | 1.9 | " | 140 | 217 |
| 4 | 4 | " | " | " | " | " | 1.8 | " | 160 | 215 |
| 5 | 5 | 134.7 | " | " | " | " | 1.9 | " | 180 | 209 |
| 6 | 6 | 162.7 | " | " | " | " | 1.9 | " | 150 | 228 |
| 7 | 7 | 135 | " | " | " | " | 1.8 | " | 190 | 209 |
| 8 | 8 | 138 | " | " | " | " | 2.0 | " | 190 | 207 |
| 9 | 1 | 144.0 | " | 222 | " | 45/36 | 1.8 | " | 150 | 215 |
| 10 | 1 | " | 555 | " | " | 45/39 | 1.7 | " | 130 | 217 |
| Comparative Ex. | Comparative Referential Example | | | | | | | | | |
| 1 | 1 | 97.3 | 370 | 148 | 100*3 | 45/38 | 1.8 | 20*4 | 180 | 157 |
| 2 | 2 | 97.3 | " | " | " | " | 1.9 | " | 200 | 159 |
| 3 | 3 | 106.7 | " | " | " | " | 2.0 | " | 190 | 170 |
| 4 | 4 | 134.7 | " | " | " | " | 2.0 | " | 170 | 205 |
| 5 | 5 | 144.0 | " | " | " | " | 1.9 | " | 150 | 212 |
| 6 | 6 | 190.6 | " | " | " | " | 2.0 | " | 190 | 258 |
|  | Referential Example | | | | | | | | | |
| 7 | 1 | 144.0 | " | " | " | " | 1.7 | — | 310 | 215 |
| 8 | 1 | " | " | — | " | 45/90 | 2.4 | 20 | 800 | 225 |

Notes:
*1 Amount containing 1 mole of phenolic hydroxy groups.
*2 Amount corresponding to 4 moles of epichlorohydrin.
*3 Amount corresponding to 1 mole of NaOH.
*4 Amount corresponding to 0.05 mole of NaOH.

EXAMPLES 11–20 AND COMPARATIVE EXAMPLES 10–16

Various glycidyl ether compounds shown in Table 3 were blended each with a phenol novolak (used as a hardener, softening point 95° C.), triphenyl phosphine (used as an accelerator), and fused silica (used as a filler) in proportions (g) as shown in Table 3. Each blend was heated and kneaded on a roll mill, and molded by pressing at 175° C. for 5 minutes. Further, each molded product was post-cured for 5 hours in a 180° C. oven to produce a cured material.

Table 3 shows the glass transition temperature, boiling water absorption (%), flexural strength, and flexural modulus of each of the cured materials.

TABLE 3

|  | Glycidyl ether compound | | Phenol novolak (g) | Triphenyl phosphine (g) | Silica (g) | Glass transition temperature (°C.) | Flexural strength (Kg/mm²) | Flexural modulus (Kg/mm²) | Boiling water absorption (%) |
|---|---|---|---|---|---|---|---|---|---|
|  | Source | Amount (g) | | | | | | | |
| Example | Example | | | | | | | | |
| 11 | 1 | 214 | 110 | 3.21 | 756 | 210 | 13.7 | 1210 | 0.78 |
| 12 | 2 | 216 | " | 3.24 | 761 | 216 | 13.9 | 1250 | 0.81 |
| 13 | 3 | 217 | " | 3.26 | 763 | 220 | 14.1 | 1320 | 0.83 |
| 14 | 4 | 215 | " | 3.23 | 758 | 208 | 13.7 | 1200 | 0.81 |
| 15 | 5 | 209 | " | 3.14 | 744 | 213 | 14.0 | 1270 | 0.84 |
| 16 | 6 | 228 | " | 3.42 | 789 | 200 | 13.0 | 1170 | 0.75 |
| 17 | 7 | 209 | " | 3.14 | 744 | 221 | 14.2 | 1280 | 0.83 |
| 18 | 8 | 207 | " | 3.11 | 740 | 214 | 13.8 | 1230 | 0.81 |
| 19 | 9 | 215 | " | 3.23 | 758 | 209 | 13.6 | 1200 | 0.77 |
| 20 | 10 | 217 | " | 3.26 | 763 | 208 | 13.7 | 1220 | 0.77 |
| Comparative Example | | | | | | | | | |
| 10 | *5 | 175 | 110 | 2.93 | 712 | 175 | 15.0 | 1320 | 0.81 |
|  | Comparative Example | | | | | | | | |
| 11 | 1 | 157 | " | 2.36 | 623 | 203 | 13.3 | 1230 | 1.03 |
| 12 | 2 | 159 | " | 2.39 | 628 | 223 | 13.7 | 1250 | 1.10 |
| 13 | 3 | 170 | " | 2.55 | 653 | 198 | 13.9 | 1300 | 0.94 |
| 14 | 4 | 205 | " | 3.08 | 735 | 193 | 14.1 | 1280 | 0.87 |
| 15 | 5 | 212 | " | 3.18 | 751 | 193 | 13.2 | 1200 | 0.76 |
| 16 | 6 | 258 | " | 3.87 | 859 | 124 | 12.7 | 1110 | 0.74 |

Note:
*5 Glycidyl ether of o-cresol novolak (manufactured by Sumitomo Chemical Co., Ltd. under the tradename of Sumi Epoxy ESCN-195, epoxy equivalent weight: 195).

What is claimed is:
1. A glycidyl ether of the formula (I):

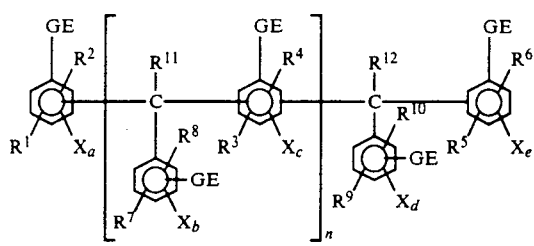

wherein each of $R^1$ through $R^6$ represents an alkyl group of from 1 to 6 carbon atoms; each of $R^7$ through $R^{12}$ represents a hydrogen atom or an alkyl group of from 1 to 4 carbon atoms; X represents a chlorine or bromine atom; GE represents a glycidyl ether group; a, b, c, d, and e are 0 or 1; and n is the average number of from 0.5 to 5.

2. A glycidyl ether of the formula (II):

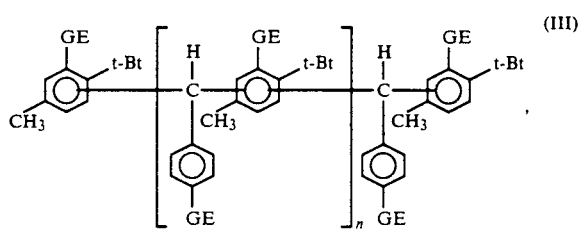

wherein each of $R^2$, $R^4$, and $R^6$ represents an alkyl group of from 3 to 6 carbon atoms; GE represents a glycidyl ether group; and n is an average number of from 0.5 to 5.

3. A glycidyl ether of the formula (III):

wherein t-Bt represents tertiary butyl; GE represents a glycidyl ether group; and n is an average number of from 0.5 to 5.

* * * * *